United States Patent
Malandain (10) Patent No.: US 7,497,024 B2
(45) Date of Patent: Mar. 3, 2009

(54) MEASUREMENT INSTRUMENT FOR PERCUTANEOUS SURGERY

(75) Inventor: Hugues F. Malandain, Mountain View, CA (US)

(73) Assignee: Kyphon SARL (CH)

( * ) Notice: Subject to any disclaimer, the term of this patent is extended or adjusted under 35 U.S.C. 154(b) by 0 days.

(21) Appl. No.: 12/134,583

(22) Filed: Jun. 6, 2008

(65) Prior Publication Data

US 2008/0229597 A1 Sep. 25, 2008

Related U.S. Application Data

(63) Continuation of application No. 11/449,854, filed on Jun. 9, 2006, now Pat. No. 7,383,639.

(60) Provisional application No. 60/698,273, filed on Jul. 12, 2005.

(51) Int. Cl.
*A61B 5/103* (2006.01)
(52) U.S. Cl. .......................................... 33/512; 33/542
(58) Field of Classification Search .................. 33/511, 33/512, 542, 544.4, 555.3, 783, 806; 600/587
See application file for complete search history.

(56) References Cited

U.S. PATENT DOCUMENTS

| | | | |
|---|---|---|---|
| 4,473,952 A | 10/1984 | Mariani | |
| 4,779,349 A * | 10/1988 | Odensten et al. | 33/806 |
| 4,993,428 A | 2/1991 | Arms | |
| 5,768,794 A | 6/1998 | Kelly | |
| 6,115,930 A | 9/2000 | Shigyo | |
| 6,427,351 B1 | 8/2002 | Matthews et al. | |
| 6,652,534 B2 | 11/2003 | Zucherman et al. | |
| 6,702,763 B2 * | 3/2004 | Murphy et al. | 600/587 |
| 6,723,058 B2 * | 4/2004 | Li | 33/512 |
| 6,902,566 B2 | 6/2005 | Zucherman et al. | |
| 7,086,172 B2 | 8/2006 | Åström | |
| 7,383,639 B2 * | 6/2008 | Malandain | 33/512 |
| 2004/0102722 A1 | 5/2004 | Naghavi | |
| 2005/0148903 A1 * | 7/2005 | Diamantopoulos | 600/587 |
| 2006/0064038 A1 | 3/2006 | Omata et al. | |
| 2006/0229716 A1 | 10/2006 | Mitrev | |

OTHER PUBLICATIONS

Wallis Operative Technique [online], Spine Next, An Abbot Laboratories Company, [retrieved on Jun. 8, 2005 or earlier], Retrieved from the Internet: <URL: www.spinenext.com/products/wallis/?idp=1 &fda=false>.
International Search Report mailed May 8, 2007, 5 pages.

* cited by examiner

*Primary Examiner*—G. Bradley Bennett
(74) *Attorney, Agent, or Firm*—Cooley Godward Kronish LLP (57) ABSTRACT

In one embodiment, an apparatus includes a projection having a tapered end portion configured to be inserted percutaneously through tissue. A measurement member is coupled to the projection and is configured to indicate a distance between adjacent anatomical structures. In another embodiment, an apparatus includes a measurement member configured to be percutaneously inserted between adjacent anatomical structures. The measurement member includes a wedge portion that is configured to contact the adjacent anatomical structures when the measurement member is moved distally between the adjacent anatomical structures. A size indicator is coupled to the wedge portion. The size indicator has a plurality of markings and is configured to be viewed on an image of the adjacent anatomical structures with the wedge portion of the measurement member disposed between the adjacent anatomical structures to indicate a distance between the adjacent anatomical structures.

20 Claims, 11 Drawing Sheets

MEASUREMENT INSTRUMENT FOR PERCUTANEOUS SURGERY

CROSS-REFERENCE TO RELATED APPLICATIONS

This application is a continuation of U.S. patent application Ser. No. 11/449,854, filed Jun. 9, 2006, now U.S. Pat. No. 7,383,639 entitled "Measurement Instrument for Percutaneous Surgery," which claims priority to U.S. Provisional Patent Application Ser. No. 60/698,273, filed Jul. 12, 2005, entitled "Measurement Instrument for Percutaneous Surgery," each of the disclosures of which are hereby incorporated by reference in its entirety.

BACKGROUND

The invention relates generally to measurement of distances between portions of hard tissue, for example, the percutaneous measurement of such distances.

Known surgical procedures exist in which information about the size of a particular opening or the distance between adjacent bones is obtained. For example, procedures are performed on joints such as the knee, shoulder, spine, etc. in which a device is placed between adjacent bones. Knowing the size of the opening or the space between the bones in which the device is to be placed prior to placement allows the surgeon to select the proper size of the material beforehand. This can reduce or prevent unnecessary trial and error during the placement portion of the procedure.

Known surgical procedures measure space between bones by using, for example, trial "spacers" of various sizes. Multiple spacers are tested in the space until the correct size is identified. Such tests with trial spacers are done using an open surgical approach to allow access to the joint. As with any open surgical procedure, however, the healing process is longer and the risk of injury and/or infection increases dramatically.

Thus, a need exists for improvements in the measurement of inter-bone spaces.

SUMMARY OF THE INVENTION

Apparatuses and methods for performing minimally-invasive medical procedures are disclosed herein. In one embodiment, an apparatus includes a projection having a tapered end portion configured to be inserted percutaneously through tissue. A measurement member is coupled to the projection and is configured to indicate a distance between adjacent anatomical structures. In another embodiment, an apparatus includes a measurement member configured to be percutaneously inserted between adjacent anatomical structures. The measurement member includes a wedge portion that is configured to contact the adjacent anatomical structures when the measurement member is moved distally between the adjacent anatomical structures. A size indicator is coupled to the wedge portion. The size indicator has a plurality of markings and is configured to be viewed on an image of the adjacent anatomical structures with the wedge portion of the measurement member disposed between the adjacent anatomical structures to indicate a distance between the adjacent anatomical structures.

DETAILED DESCRIPTION

In one embodiment, an apparatus includes a projection having a tapered end portion configured to be inserted percutaneously through tissue. A measurement member is coupled to the projection and is configured to indicate a distance between adjacent anatomical structures (e.g., adjacent bone structures), such as, for example, adjacent spinous processes.

As used in this specification and the appended claims, the singular forms "a," "an" and "the" include plural referents unless the context clearly dictates otherwise. Thus, for example, "a marking" is intended to mean one or more markings, or a combination of markings. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the end of a medical device inserted inside the patient's body would be the distal end of the medical device, while the end of the medical device outside the patient's body would be the proximal end of the medical device.

Figure 1:
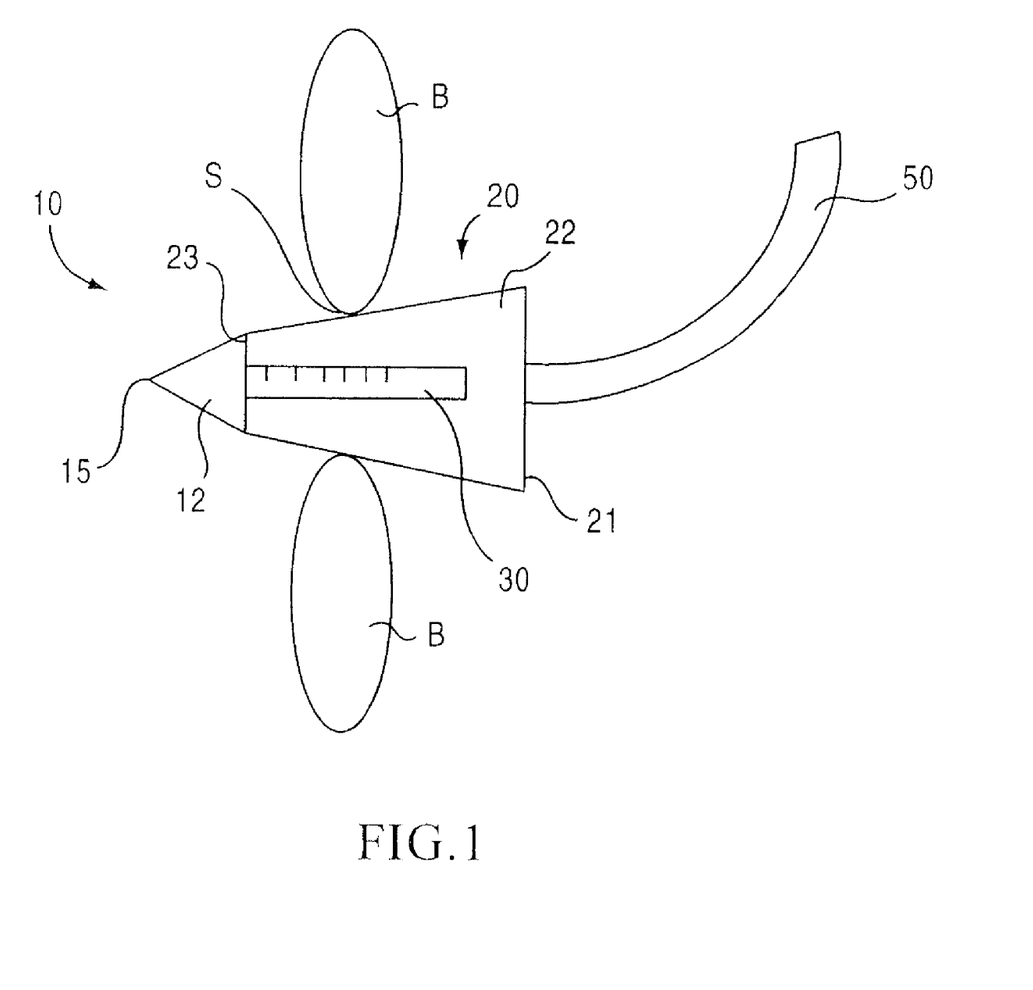
FIG. 1 is a schematic illustration of a medical device according to an embodiment of the invention between two adjacent bones.

FIG. 1 is a schematic illustration of a medical device 10 according to an embodiment of the invention between adjacent bones B (e.g., spinous processes). The medical device 10 includes a projection 12 having a tapered end portion 15. The tapered end portion 15 can include, for example, a tapered tip. A measurement member 20 is coupled to the projection 12. In some embodiments, the measurement member 20 is unitarily or monolithically formed with the projection 12. The measurement member 20 includes a tapered wedge portion 22 having a proximal end 21 and a distal end 23. The measurement member 20 also includes a size indicator 30 that provides an indication of the distance between the adjacent bones B. A handle 50 is coupled to the measurement member 20 to facilitate manipulation of the measurement member 20 from outside the body in which the measurement member 20 is positioned.

In use, the tapered end portion 15 of the projection 12 is inserted into tissue percutaneously to provide access to a space S between adjacent anatomical structures, such as bones B shown in FIG. 1. As the measurement member 20 is disposed between the adjacent bones B, the bones B may be slightly distracted by the measurement member 20. For example, depending on the force used to insert and position the measurement member 20 and/or depending on the material used to form the measurement member 20, the measurement member 20 can distract the bones B. In other embodiments, the measurement member dies not distract the bones B. Once the measurement member 20 is properly positioned, the size of the space S is measured as described below with reference to various embodiments.

Figure 2:
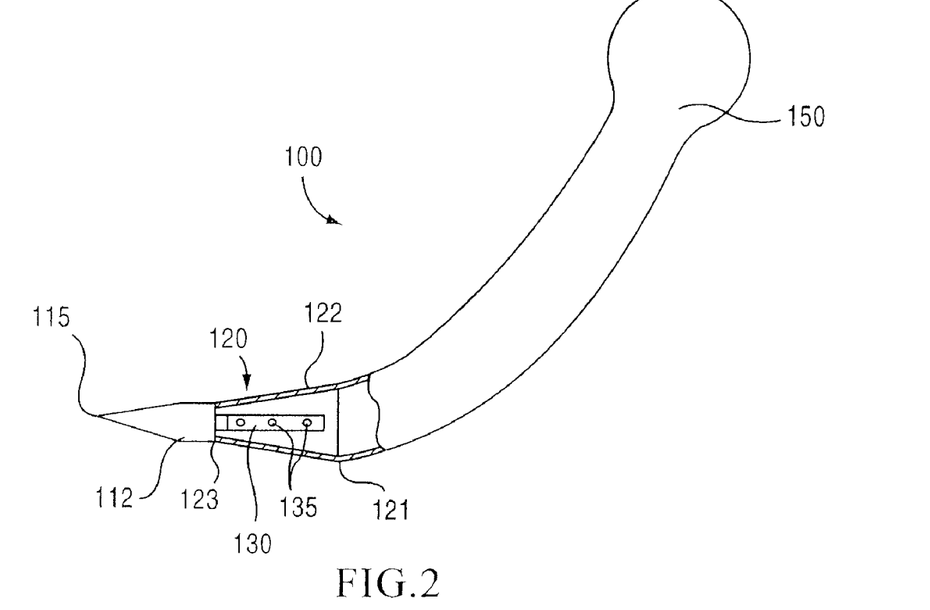
FIG. 2 is a partial cross-sectional side view of a medical device according to an embodiment of the invention.

FIG. 2 illustrates a medical device 100 according to an embodiment of the invention. The medical device 100 includes a projection 112 having a tapered end portion 115. A measurement member 120 is coupled to the projection 112. The measurement member 120 includes a tapered wedge portion 122 having a proximal end 121 and a distal end 123. A handle 150 is coupled to a portion of the measurement member 120 to facilitate manipulation of the measurement member 120 from outside the body in which the measurement member 120 is positioned. In some embodiments, the tapered wedge portion 122 is radiolucent such that the tapered wedge portion 122 is not visible under fluoroscopy or other suitable imaging modalities. In other embodiments, the tapered wedge portion 122 is radiopaque such that the tapered wedge portion 122 is visible under an imaging modality. The tapered wedge portion 122 is conically shaped to facilitate insertion between adjacent bones. In some embodiments, the tapered wedge portion 122 is made from a material of suitable hardness to distract adjacent bones when sufficient force is applied by the user.

Figure 3:
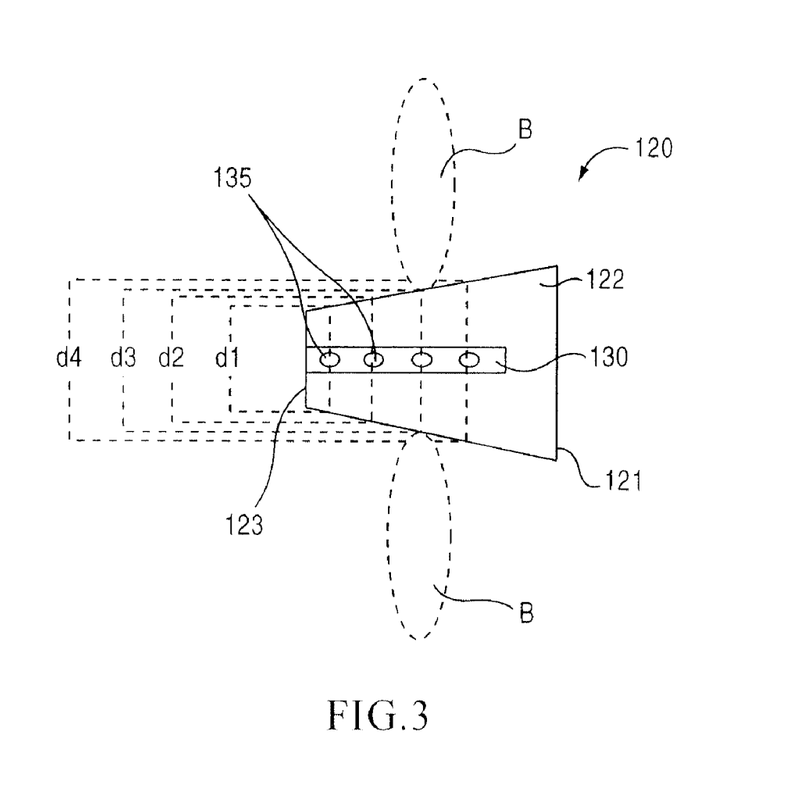
FIG. 3 is a side view of a portion of a medical device according to an embodiment of the invention.

The measurement member 120 includes a size indicator 130 that provides an indication of the distance between adjacent bones. In some embodiments, the size indicator 130 is positioned inside the tapered wedge portion 122 of the measurement member 120. The size indicator 130 includes markings 135 along its length that correspond to associated diameters of the tapered wedge portion 122. For example, as illustrated in FIG. 3, the markings 135 correspond to diameters d1, d2, d3 and d4 of the tapered wedge portion. In this embodiment, the size indicator 130 is radiopaque such that it is visible under fluoroscopy. While the size indicator 130 illustrated in FIG. 3 includes four markings 135, one or more markings can be used in other embodiments.

In some embodiments, the markings 135 are constructed with radiopaque materials and disposed on the size indicator 130 such that the markings 135 can be seen under fluoroscopy. In other embodiments, the markings 135 are configured as openings or notches defined along the length of the size indicator 130; in this embodiment, the opening or notches can be identified when the size indicator is seen under fluoroscopy.

In use, the medical device 100 is inserted percutaneously in a distal direction between adjacent bones B until the wedge portion 122 of measurement member 120 encounters sufficient resistance such that the user discontinues the distal movement, as shown in FIG. 3. This can be before distraction of the bones B or sometime after the bones B are distracted to some extent, Once properly inserted between the adjacent bones B, fluoroscopy (or another imaging modality) can be used to image the medical device 100 in position. The fluoroscopic image shows the position of the size indicator 130 between the bones B to indicate the distance between the adjacent bones B. For example, referring to FIG. 3, the distance between the adjacent bones B is the distance d3. Following this example, a corresponding fluoroscopic image shows that the third marking 135 is disposed between bones B; by identifying the third marking 135, the distance d3 is identified. Once the distance between the adjacent bones B is known, the medical device 100 can be removed and an appropriate implant or spacer can be selected and inserted between the adjacent bones B.

The actual size of the tapered wedge portion 122 depends upon its intended use. For example, if the measurement member 100 is to be used to measure the distance between adjacent spinous processes, the diameter of the tapered wedge portion 122 can range from 1 mm to 20 mm. If the measurement member 120 is to be used to measure the distance between different bones, other diameters of the tapered wedge portion can be appropriate.

In some embodiments, the handle 150 of the medical device 100 is substantially straight. In other embodiments, the handle 150 is curved. To facilitate access to bones in certain situations, a curved handle 150 (as shown in FIG. 2) may be more desirable than a straight handle. For example, a curved handle can be used to access the space between the spinous processes of the L4-L5 vertebrae to avoid the iliac crest. Alternatively, a straight handle can be used to access spinous processes of the higher lumbar region. In some embodiments, the handle is flexible or bendable to further facilitate movement of the medical device 100 within the patient's body.

Figure 4:
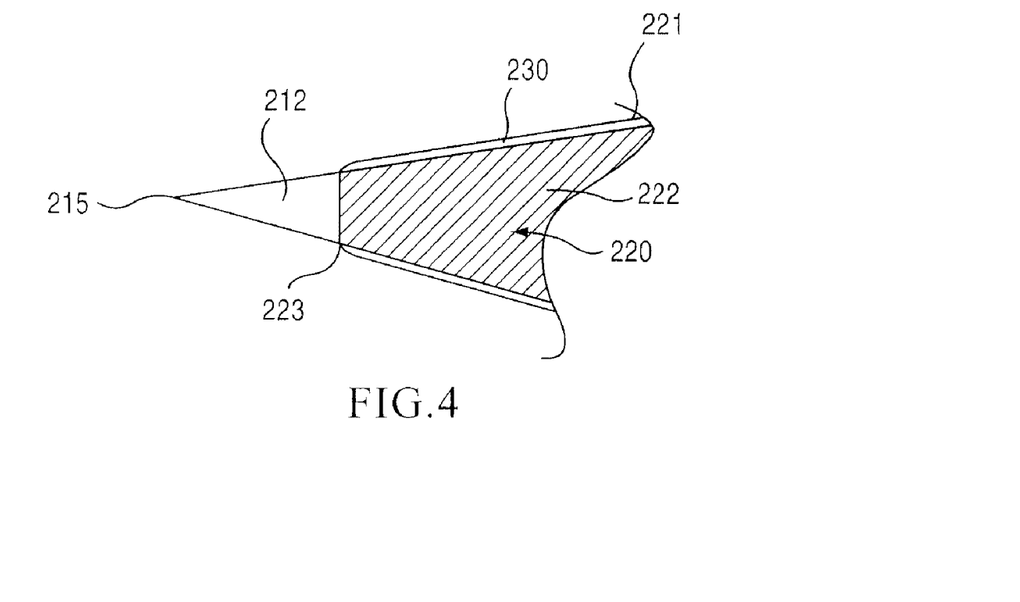
FIG. 4 is a partial cross-sectional side view of a portion of a medical device according to another embodiment of the invention.

A portion of a medical device 200 according to another embodiment of the invention is illustrated in FIG. 4. The medical device 200 includes a projection 212 having a tapered end portion 215. A measurement member 220 is coupled to the projection 212. The measurement member 220 includes a tapered wedge portion 222 having a proximal end 221 and a distal end 223. A handle (not illustrated in FIG. 4) can be coupled to the measurement member 220 to facilitate manipulation of the measurement member 220 from outside the body in which the measurement member 220 is positioned.

In this embodiment, the measurement member 220 includes a film coating 230 on the outer surface of the tapered wedge portion 222. The film coating 230 is, for example, a pressure-sensitive film that is configured to be altered as the measurement member 220 is inserted between adjacent bones. As the film coating 230 contacts ligaments and/or bone, a witness mark (not illustrated) will be left on the film coating 230 in the form of, for example, a scratch, an indentation, and/or a color change, etc. When the medical device 200 is removed from the patient, the witness mark on the film coating 230 can indicate the point at which distal movement of the wedge portion 222 ceased. This point is associated with the distance between the adjacent bones.

In use, the measurement member 220 is inserted between adjacent bones until the wedge portion 222 of the measurement member 220 stops (e.g., measurement member 120 encounters sufficient resistance such that the distal movement of the measurement member 120 ceases). The measurement member 220 is then withdrawn from the patient's body. Once withdrawn, the witness mark will indicate the depth of insertion of the measurement member 220. The corresponding size of the measurement member 220 or width transverse to the direction of movement (e.g., the diameter of the measurement member 220 if cylindrical in shape), can then be obtained based on the witness mark. In some embodiments, the measurement member 220 includes size indicators on the measurement member itself (e.g., size markings on the outside of the device). In other embodiments, a separate instrument can be used to measure the transverse size of the measurement member 220 where the witness mark is located.

Figure 5:
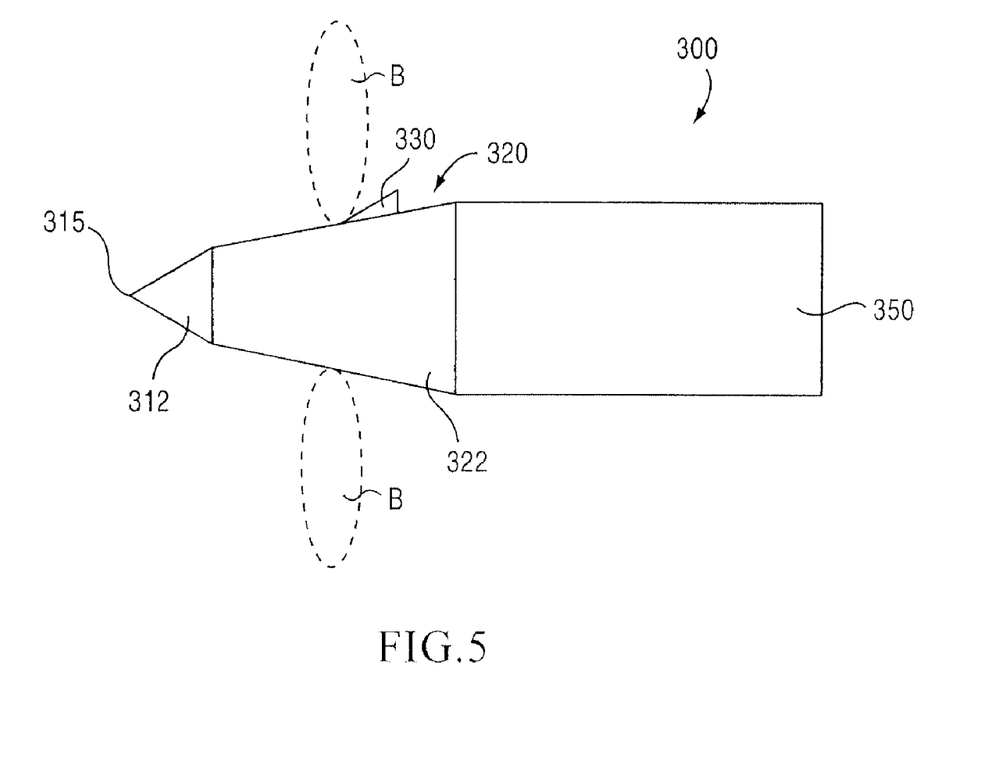
FIG. 5 is a side view of a medical device according to a further embodiment of the invention.

FIG. 5 illustrates a medical device 300 according to another embodiment of the invention. The medical device 300 includes a projection 312 having a tapered end portion 315. A measurement member 320 is coupled to a portion of the projection 312. The measurement member 320 includes a tapered wedge portion 322 having a proximal end 321 and a distal end 323. A handle 350 is coupled to or a portion of the measurement member 320 to facilitate manipulation of the measurement member 320 from outside the body in which the measurement member 320 is positioned.

Figure 6:
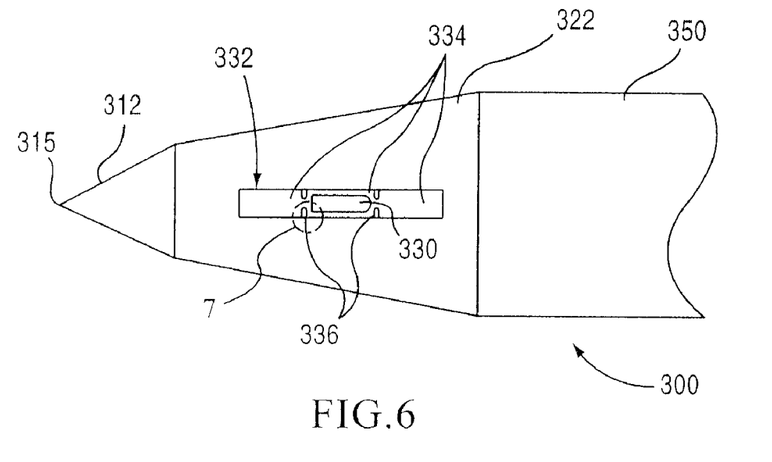
FIG. 6 is a top view of the medical device of FIG. 5.

In this embodiment, the measurement member 320 includes a size indicator tab 330 that is movably coupled to the tapered wedge portion 322. The size indicator tab 330 can be, for example, a protrusion movably coupled to the tapered wedge portion 322 via a slot or groove 332 in tapered wedge portion 322. This slot or groove 332 allows movement of the size indicator tab 330 along the wedge portion 322 in the proximal direction only (see FIG. 6). For example, the slot 332 of the tapered wedge portion 322 can have a series of openings 334 disposed on an outer surface of the tapered wedge portion 322 separated by one or more detent 336, as shown in FIG. 6. In some embodiments, the openings are wedge-shaped with each opening oriented with a narrower portion in the distal direction and a wider portion in the proximal direction.

Figure 7:
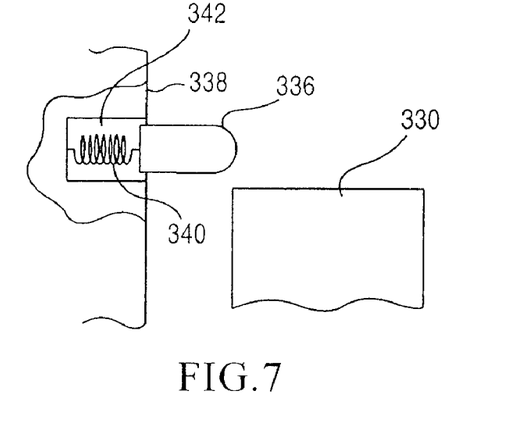
FIG. 7 is an enlarged view of a portion of the medical device of FIG. 6.
Figure 8:
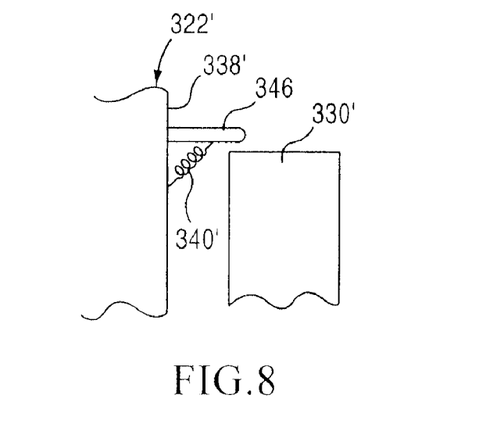
FIG. 8 is a detent according to an alternative embodiment of the invention.

The detents 336 are configured such that the size indicator tab 330 can be pushed through the openings 334 in a proximal direction, but cannot move back in the distal direction through the openings 334. For example, as shown in FIG. 7 the detents 336 can be a plunger-type spring-loaded mechanism coupled to a side wall 338 of the wedge-shaped portion 322, as shown in FIG. 7. The detents 336 are biased into a substantially perpendicular position relative to the side wall 338 and inwardly toward a center of the opening 334 by a spring 340. The detents 336 are pushed into a pocket 342 defined by the side wall 338 as the size indicator tab 330 is pushed through one of the opening 334. When the detents 336 return back to the spring-biased position, the size indicator tab 330 cannot move back distally through the opening 334 without applying a force in a distal direction. The size indicator tab 330 can, in alternative embodiments, have a different shape, size and/or configuration. For example, in some embodiments, a size indicator tab can have a quarter or half moon shape when viewed from a top side. In such a configuration, the size indicator tab can be rounded on a proximal end and have a sharp corner on a distal end, such that the rounded end can push through the detents when the wedge portion is moved in a proximal direction, but the sharp corner on the distal end does not allow the size indicator tab to pass back through the detents in a distal direction. In other embodiments, the detents can include other spring-loaded mechanisms such as a pivoting arm mechanism 344, as shown in FIG. 8. In this embodiment of a detent, a pivot arm 346 is pivotally coupled to a side wall 338' of a wedge-shaped portion 322'. A spring 340' is coupled to the pivot arm 346 and to the side wall 338' that biases the pivot arm into a substantially perpendicular position relative to the side wall 338'. In alternative embodiments, the detents can be shaped to allow only proximal movement of the tab through the detent. For example, a distal side of the detent can be rounded to allow the tab to push through the detent, and a proximal side of the detent can include a substantially sharp corner that does not allow the tab to move back distally through the detent.

In use, the measurement member 320 is inserted in a distal direction between adjacent bones until the distal movement of the tapered wedge portion 322 of measurement member 320 encounters sufficient resistance by the bones such that the distal movement of the measurement member 320 ceases. This resistance can be before distraction of the adjacent bones or sometime after the bones are distracted to some extent. The measurement member 320 is then withdrawn. When the measurement member 320 is inserted between adjacent bones, the size indicator tab 330 is in a first position along the tapered wedge portion 322 and then when the size indicator tab 330 engages the adjacent bones the size indicator tab 330 is moved proximally along the tapered wedge portion 322 to a second position (e.g., when the tapered wedge portion 330 encounters sufficient resistance and the distal movement of the measurement member 320 ceases). When the measurement member 320 is withdrawn, the size indicator tab 330 remains in place in the second position to indicate the depth of insertion of the measurement member 320. The corresponding width of the measurement member 320 at the particular depth of insertion can then be obtained.

Figure 9:
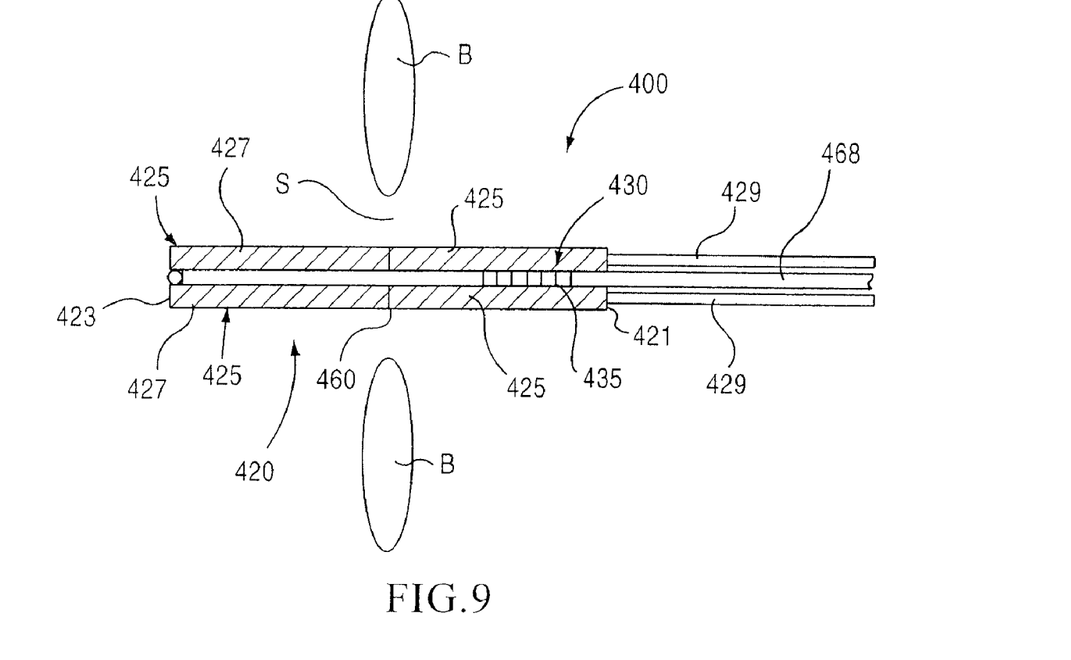
FIG. 9 is a side view partially in cross-section of a medical device according to another embodiment of the invention in a first configuration.
Figure 10:
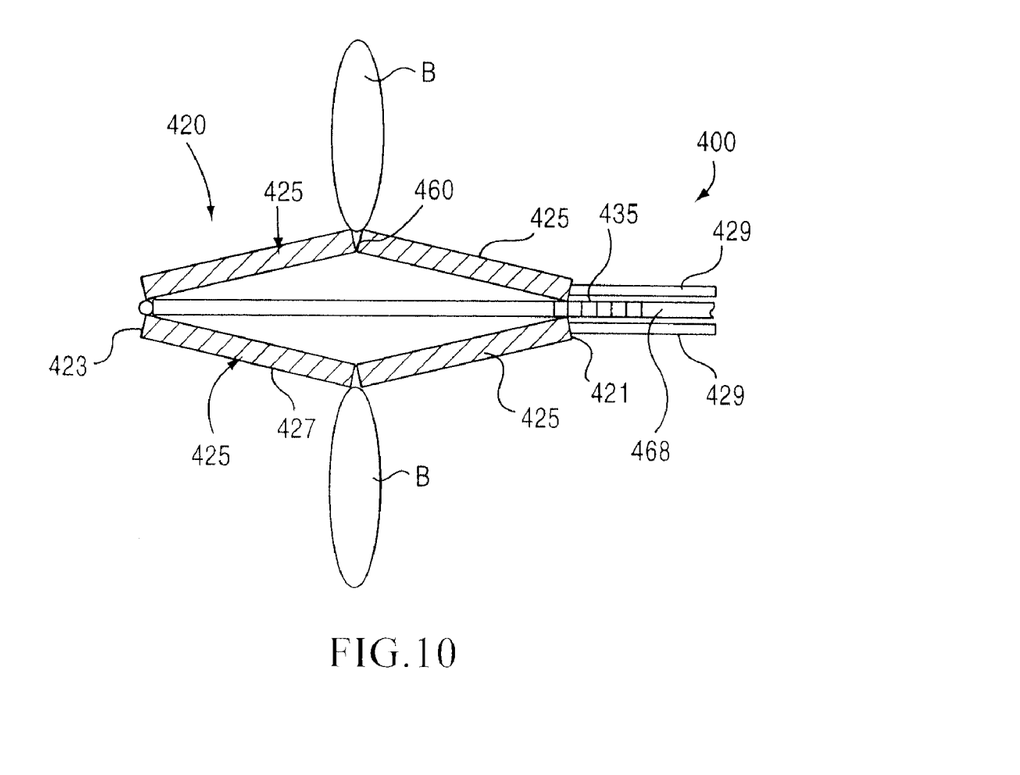
FIG. 10 is a side view partially in cross-section of the medical device illustrated in FIG. 9 in a second configuration.

FIGS. 9 and 10 illustrate a medical device 400 according to an embodiment of the invention. The medical device 400 includes a measurement member 420 having a proximal end 421 and a distal end 423. The measurement member 420 includes expandable members 425 that are configured to move from a first configuration as illustrated in FIG. 9, to a second configuration as illustrated in FIG. 10. The expandable members 425 include an expandable portion 427 and an elongate portion 429. To move the expandable members 425 from the first configuration to the second configuration, an expansion actuator 468 coupled to the expandable members 425 is drawn back (i.e., distally) through the measurement member 420, while holding the elongate portion 429 of the expandable members 425 stationary, such that the expandable portions 427 collapse at a mid-point 460, as shown in FIG. 10. The mid-point 460 can be, for example, a hinged portion of the expandable portions 427. Alternatively, the expandable portions 425 can include two portions that are pivotally coupled at the mid-point 460.

Figure 11:
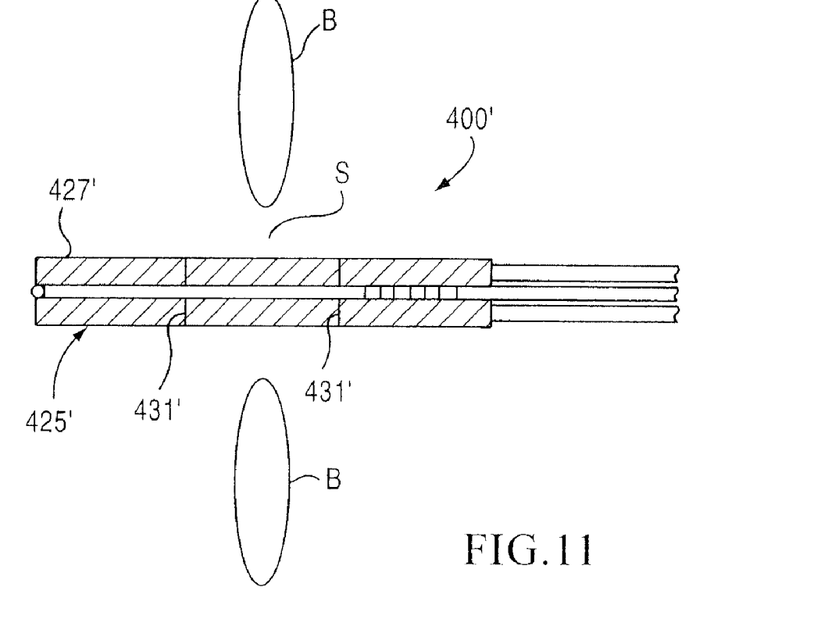
FIG. 11 is a side view partially in cross-section of a medical device according to another embodiment of the invention in a first configuration.
Figure 12:
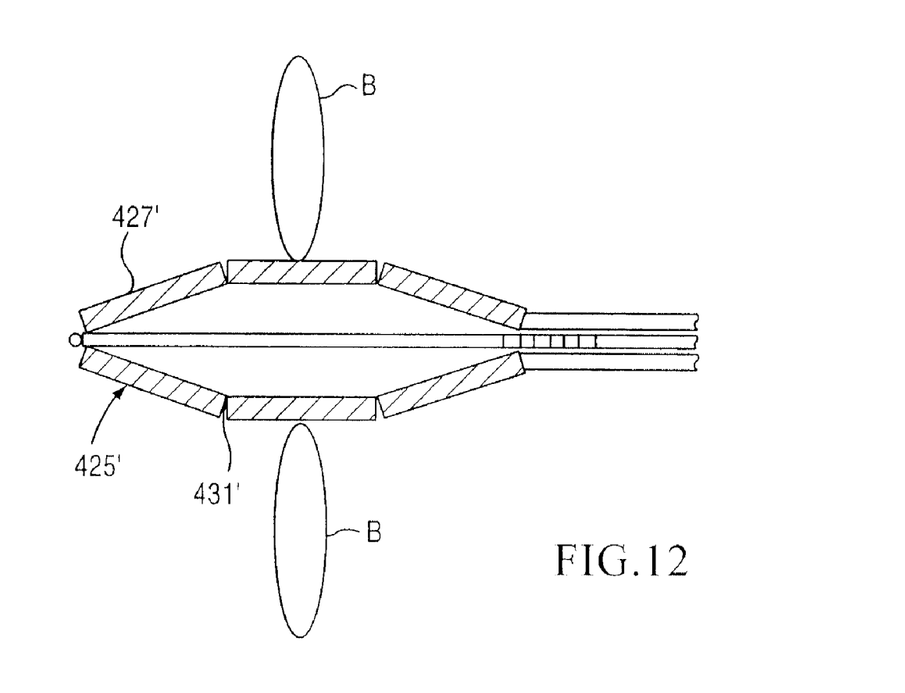
FIG. 12 is a side view partially in cross-section of the medical device illustrated in FIG. 11 in a second configuration.

In another embodiment, the expandable members can have a different configuration than described above. For example, a medical device 400' can include an expandable member 425' having three expandable portions 427' as shown in FIGS. 11 and 12. The three expandable portions 427' can be coupled together, for example, with hinged or pivot couplings 431'. In such an embodiment, the expandable members 425' can be moved from a first configuration, as shown in FIG. 11, to a second configuration, as shown in FIG. 12, in a similar manner as described above for medical device 400.

Figure 13:
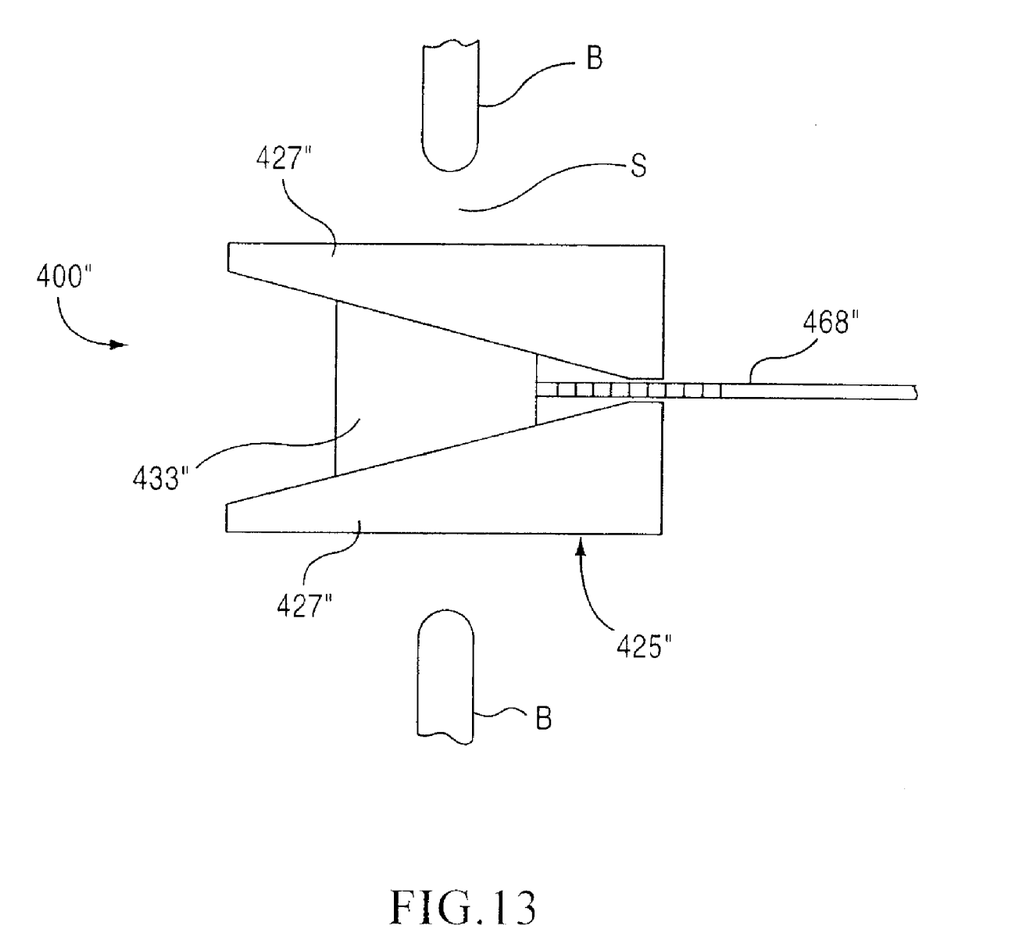
FIG. 13 is a side view partially in cross-section of a medical device according to another embodiment of the invention in a first configuration.
Figure 14:
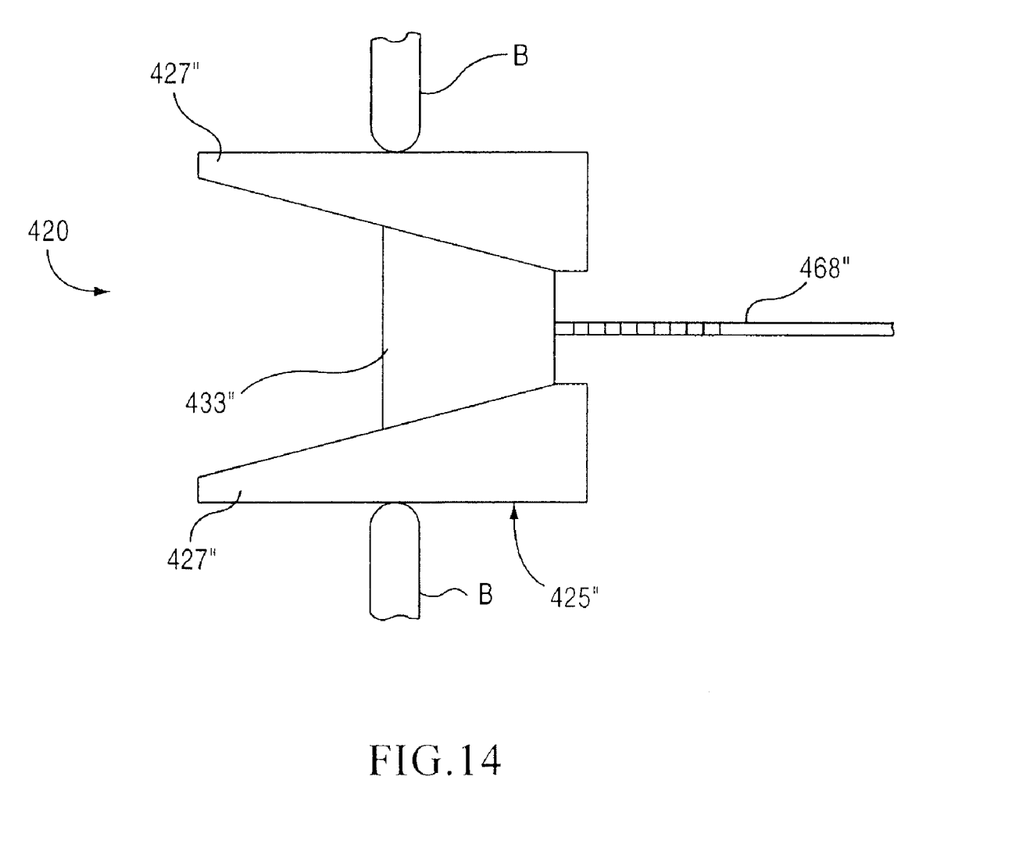
FIG. 14 is a side view partially in cross-section of the medical device illustrated in FIG. 13 in a second configuration.

In yet another embodiment, as shown in FIGS. 13 and 14, a medical device 400" can include expandable members 425" that do not include expandable portions that are hinged or pivotally coupled. In this embodiment, the expandable members 425" have expandable portions 427" that define an interior volume, in which an actuating block 433" is positioned. The expandable members 425" can be moved between a collapsed configuration, as shown in FIG. 13, and an expanded configuration, as shown in FIG. 14. To move the expandable members 425" from the collapsed configuration to the expanded configuration, an expansion actuator 468"

that is coupled to the actuating blocks 433" is moved proximally, which in turn pulls the actuating block 433" proximally. As the actuating block 433" is moved in the proximal direction, the block 433" exerts a force on the inner walls of the expandable portions 427" and causes the expandable portions 427" to be pushed or forced in a direction away from each other, as shown in FIG. 14. Other configurations for expandable portions 425" can be used. For example, the expandable portions and the actuating block can each have a different shape and/or size. Also, an expansion member can include more than one actuating block. In addition, the expansion actuator can have a different configuration. For example, a distal end of the expansion actuator can include a threaded portion to threadedly couple to the actuating block(s). In such an embodiment, the actuating block(s) can be actuated by turning the expansion actuator.

Referring back to FIGS. 9 and 10, the measurement member 420 includes a size indicator 430 on the expansion actuator 468 that provides an indication of the distance between adjacent bones B. In some embodiments, the size indicator 430 is positioned between the expandable members 425. The size indicator 430 includes markings 435 along its length that correspond to the distance the expansion actuator 468 is moved. The distance that the expansion actuator 468 is moved corresponds to an associated distance between opposing expandable members 425. In some embodiments, the size indicator 430 is radiopaque such that it is visible under fluoroscopy, or other imaging modalities. In another embodiment, the size indicator can be a witness mark similar to that discussed above. In yet another embodiment, the markings are visible outside of the body. For example, the markings can be located on a portion of expansion actuator 468 that extends outside of the patient's body. In such an embodiment, no imaging is necessary to determine the distance the expansion actuator is moved.

In use, the medical device 400 is inserted percutaneously between adjacent bones in the first configuration until the mid-point 460 of the measurement member 420 is approximately adjacent the bones B (i.e., in the space S between the bones B). Once properly inserted, the expandable members 425 are moved to the second configuration as illustrated in FIG. 10. When in the second configuration, an image is taken of the medical device 400. The image shows the position of the markings 435 on size indicator 430 to indicate the distance the expansion actuator 468 was moved. Once the distance between the adjacent bones is known, an appropriate implant or spacer can be selected and inserted. After the distance between adjacent bones B is known, the measurement member 420 is moved to the first configuration and removed.

Figure 15:
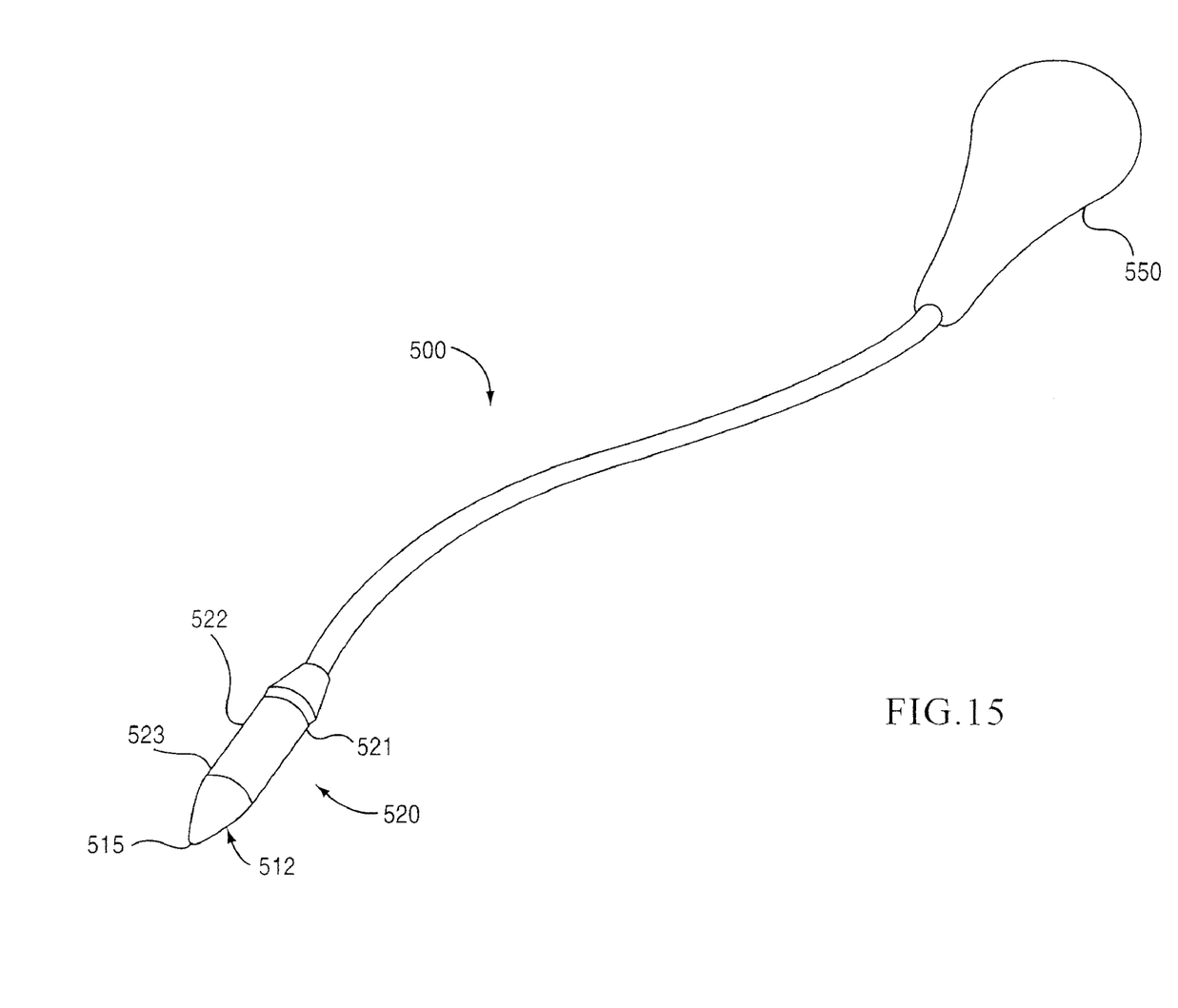
FIG. 15 is a side view of a medical device according to another embodiment of the invention.
Figure 16:
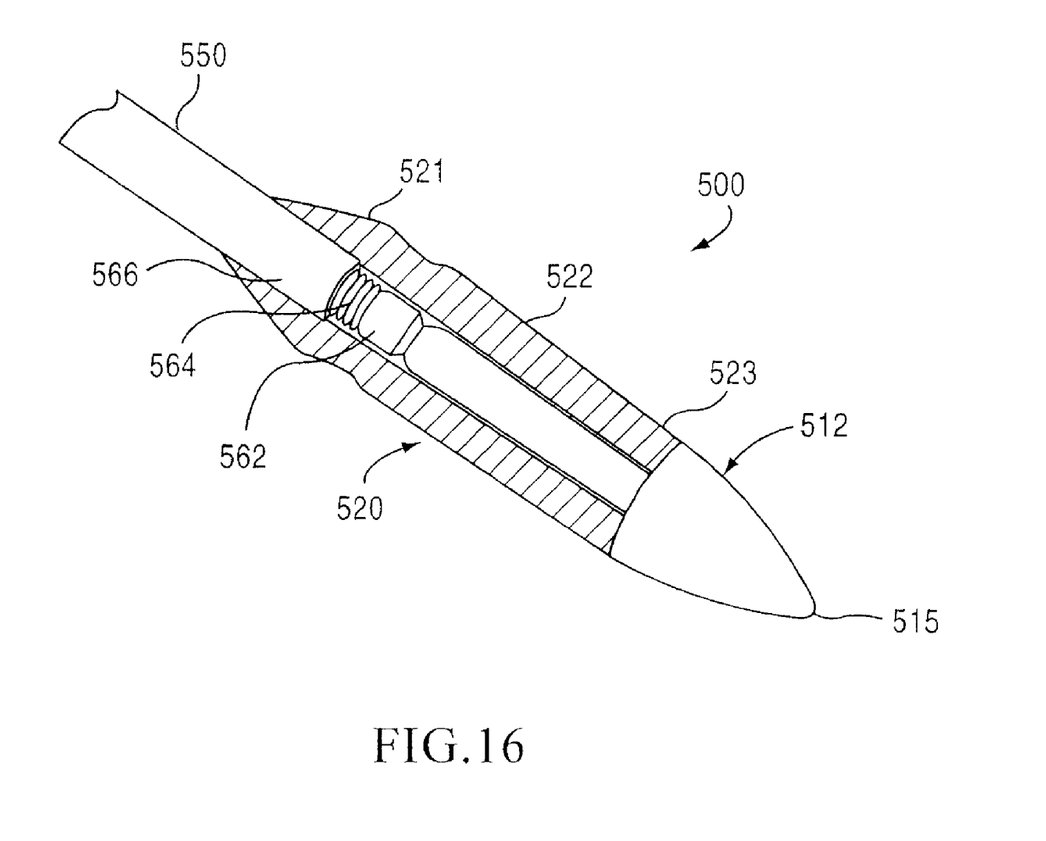
FIG. 16 is a partial cross-sectional view of a portion of the medical device of FIG. 15.

FIGS. 15 and 16 illustrate a medical device according to another embodiment of the invention. A medical device 500 includes a projection 512 having a tapered end portion 515. The medical device 500 also includes a measurement member 520 coupled to the projection 512 or formed monolithically with the projection 512. The measurement member 520 includes a tapered wedge portion 522 having a proximal end 521 and a distal end 523. A handle member 550 is coupled to the measurement member 520 to facilitate manipulation of the measurement member 520 from outside the body in which the measurement member 520 is positioned.

The measurement member 520 can also include a size indicator (not shown in FIGS. 15 and 16) that provides an indication of the distance between adjacent bones. Any of the previously described size indicators can be used in this embodiment. In this embodiment, the measurement member 520 is threadedly coupled to the handle 550. The measurement member 520 includes a connector 562 disposed within a lumen defined by the measurement member 520, as shown in FIG. 16. The handle 550 includes a threaded portion 564 on a distal end portion 566 to which the connector 562 can be releasably and threadedly coupled. This threaded coupling allows the measurement member 520 to be removed and replaced as desired. For example, multiple measurement members 520 can be provided in a kit, and a user can select the particular measurement member 520 appropriate in size or material hardness for a particular application. This type of threaded coupling can also be included on any of the previously described embodiments.

Figure 17:
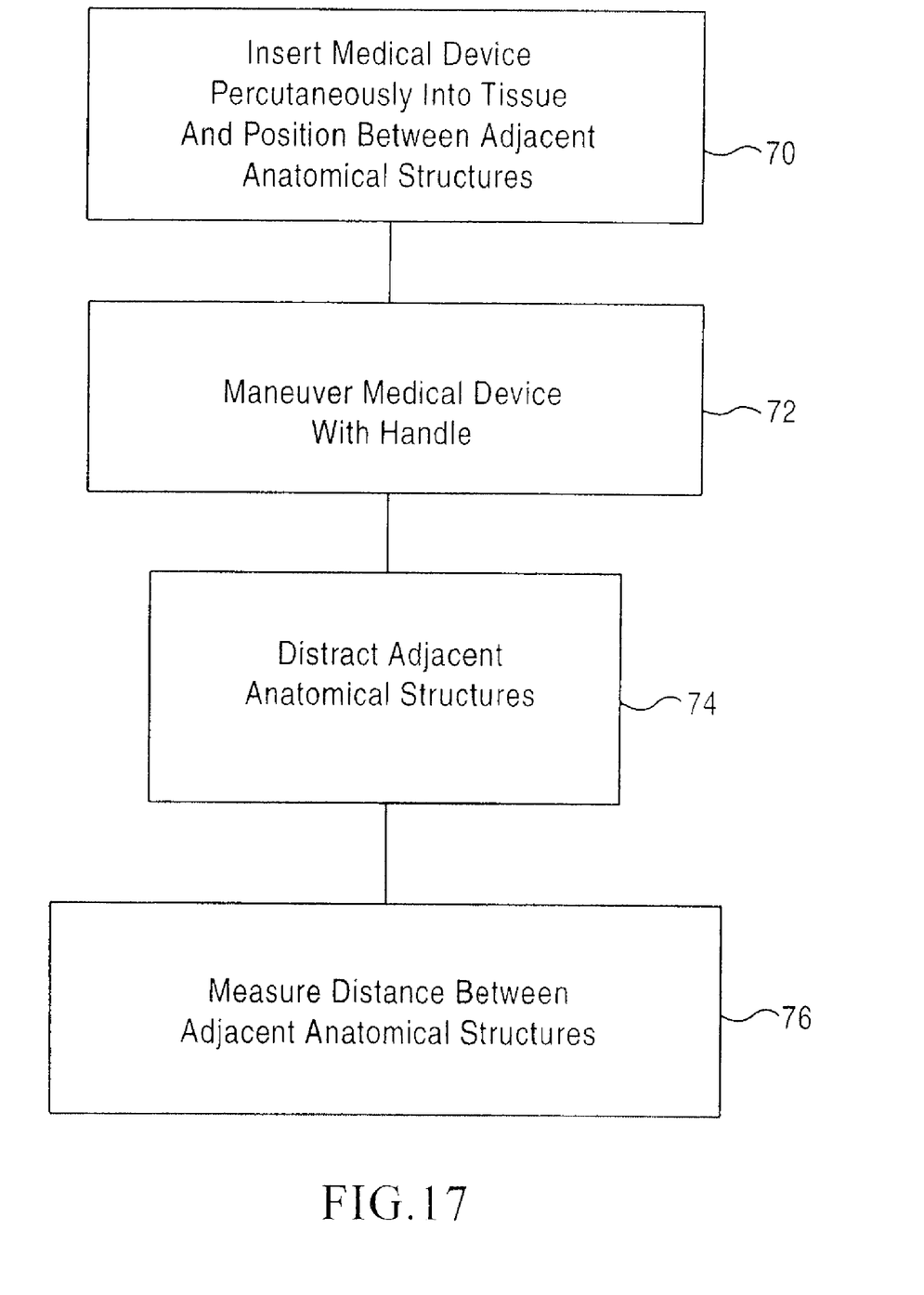
FIG. 17 is a flow chart of a method according to en embodiment of the invention.

FIG. 17 is a flow chart illustrating a method according to an embodiment of the invention. A method includes at 70 inserting percutaneously into a tissue, a medical device, having a measurement member such that the measurement member is positioned between adjacent anatomical structures. For example, the measurement member can be positioned between adjacent spinous processes. In some embodiments, a projection coupled to the measurement member is used to penetrate the tissue. In other embodiments, a separate tool is used to penetrate the tissue prior to inserting the medical device. The medical device can include a handle that extends outside of the patient's body and that can be used to maneuver the measurement member to the position between anatomical structures, as indicated at 72. In some embodiments, when the measurement member is positioned between the anatomical structures, the measurement member optionally distracts the anatomical structures as indicated at 74.

At 76, a distance can be measured between the adjacent anatomical structures. The measuring of this distance can include a variety of different procedures depending on the particular embodiment. For example, in some embodiments, the measuring of this distance between the adjacent anatomical structures includes viewing a radiopaque size indicator that is coupled to the measurement member on an imaging device. In other embodiments, the measuring a distance between the adjacent anatomical structures includes measuring a diameter or width of the measurement member. In other embodiments, the measuring includes measuring a location of a witness mark on a film coating that is coupled to the measurement member. For example, the film coating can be disposed on an outer surface of the measurement member such that as the measurement member is positioned between the adjacent anatomical structures the adjacent anatomical structures contact the film coating and leave a witness mark.

In still other embodiments, the measurement member can include a movable tab, and the measuring a distance includes measuring a distance that the tab moved during the positioning of the measurement member between the adjacent anatomical structures. In yet other embodiments, the measurement member can include a first expandable member and a second expandable member, and the positioning the measurement member can include moving the first expandable member and the second expandable member until the first expandable member contacts one of the adjacent anatomical structures and the second expandable member contacts the other of the adjacent anatomical structures. In such an embodiment, the measuring a distance includes measuring a distance that the first expandable member and the second expandable member moved during the positioning of the measurement member between adjacent anatomical structures.

The various components of the medical device 10 (110, 210, 310, 410, 510) can be constructed or formed with any suitable biocompatible materials. For example, suitable biocompatible plastics and/or metals can be used.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

For example, although the embodiments of the medical device described above are primarily described as being used to measure the distance between adjacent spinous processes, in alternative embodiments, the medical device is used to measure the space between the bones of the leg, arm or other bodily structure where it is desirable to maintain a particular spacing. In fact, the medical device can be used to measure the spacing between any two biological structures (e.g., hard tissue), that is relatively harder than the intervening soft tissue.

Although described as being imaged with a fluoroscope, in alternative embodiments, the medical device can be imaged using any imaging modality such as, for example, magnetic resonance imaging (MRI), computed tomography (CT) scan, x-ray, and/or ultrasound.

In addition, although described above as having a tapered wedge portion with a circular cross section, the measurement member can have any shape, such as square, hexagon, etc. Additionally, although the markings 135 are generally illustrated as being of similar size and shape, in alternative embodiments, the markings 135 may be different sizes and shapes.

Furthermore, although the medical device is described as including a projection having a tapered end portion, in alternative embodiments, the measurement member may not include a projection having a tapered end portion. For example, the measurement member can be delivered through a cannula that is positioned adjacent a space between adjacent bones.

What is claimed is:

1. An apparatus, comprising:
a measurement member configured to be disposed in a space between adjacent anatomical structures, the measurement member configured to be moved between a collapsed configuration and an expanded configuration; and
a size indicator coupled to the measurement member, the size indicator having a plurality of markings, the size indicator configured to be remotely viewed while the measurement member is disposed in the space between the adjacent anatomical structures to indicate a distance between the adjacent anatomical structures.

2. The apparatus of claim 1, further comprising:
a tapered projection coupled to the measurement member, the tapered projection configured to penetrate biological tissue.

3. The apparatus of claim 1, wherein the measurement member includes a tapered wedge portion configured to move when the measurement member is moved between the collapsed configuration and the expanded configuration.

4. The apparatus of claim 1, wherein each marking from the plurality of markings corresponds to a distance the measurement member traveled when moved from its collapsed configuration to its expanded configuration.

5. The apparatus of claim 1, wherein the measurement member includes an expandable member including a first expandable portion pivotally coupled to a second expandable portion, the first expandable portion and the second expandable portion being movable between a collapsed configuration and an expanded configuration.

6. The apparatus of claim 1, wherein the measurement member includes a first expandable portion, a second expandable portion and a wedge member slidably coupled to the first expandable portion and the second expandable portion,
the first expandable portion and the second expandable portion each configured to be moved from a collapsed configuration to an expanded configuration when the wedge member is moved axially relative to the first expandable portion and the second expandable portion,
when in the expanded configuration, the first expandable portion configured to contact one of the adjacent anatomical structures and the second expandable portion configured to contact the other of the adjacent anatomical structures.

7. The apparatus of claim 1, further comprising:
an elongate member coupled to the measurement member, the size indicator disposed on the elongate member, the measurement member configured to move relative to the elongate member such that a distance the measurement member moves relative to the elongate member corresponds to the distance between the adjacent anatomical structures.

8. An apparatus, comprising:
a measurement member configured to be percutaneously inserted between adjacent anatomical structures while in a first configuration;
an actuator coupled to the measurement member, the actuator configured to exert an axial force on the measurement member to move the measurement member to a second configuration, the measurement member being in contact with the adjacent anatomical structures when in the second configuration; and
a size indicator disposed at a location on the actuator associated with a portion of the measurement member, the size indicator including a plurality of markings configured to indicate a distance between the adjacent anatomical structures.

9. The apparatus of claim 8, further comprising:
a projection coupled to the measurement member, the projection including a sharp tip configured to penetrate biological tissue.

10. The apparatus of claim 8, wherein the plurality of markings are radiopaque.

11. The apparatus of claim 8, wherein each marking from the plurality of markings corresponds to a distance the measurement member traveled when moved from its first configuration to its second configuration.

12. The apparatus of claim 8, wherein the measurement member includes a first expandable member and a second expandable member, the first expandable member and the second expandable member being in a collapsed configuration when the measurement member is in the first configuration,
the first expandable member and the second expandable member each configured to be moved from the collapsed configuration to an expanded configuration when the measurement member is moved to the second configuration such that the first expandable member contacts one of the adjacent anatomical structures and the second expandable member contacts the other of the adjacent anatomical structures.

13. The apparatus of claim 8, wherein the measurement member includes a first expandable portion, a second expandable portion and a wedge member slidably coupled to the first expandable portion and the second expandable portion, the first expandable portion and the second expandable portion configured to be moved from a collapsed configuration to an expanded configuration when the wedge member is moved axially relative to the first expandable portion and the second expandable portion, when in the second configuration, the first expandable portion configured to contact one of the adjacent anatomical structures and the second expandable portion configured to contact the other of the adjacent anatomical structures.

14. A method, comprising:

inserting a medical device including a measurement member while in a first configuration percutaneously into a tissue such that the measurement member is positioned in a space between adjacent anatomical structures, the measurement member including a size indicator remotely viewable on an imaging device;

applying an axial force to the measurement member such that the measurement member moves from the first configuration to a second configuration; and after the applying, providing an indication of a distance between the adjacent anatomical structures.

15. The method of claim 14, wherein during the applying, the measurement member distracts the adjacent anatomical structures.

16. The method of claim 14, wherein during the inserting, a projection coupled to the measurement member penetrates the tissue.

17. The method of claim 14, wherein the size indicator includes a plurality of radiopaque markings, the providing includes providing an image of the plurality of markings on an imaging device.

18. The method of claim 14, wherein the measurement member includes a first expandable member and a second expandable member, the applying includes moving the first expandable member and the second expandable member until the first expandable member contacts one of the adjacent anatomical structures and the second expandable member contacts the other of the adjacent anatomical structures.

19. The method of claim 14, wherein the measurement member includes a first expandable member and a second expandable member, the medical device further includes an elongate actuator coupled to the measurement member, the applying includes pulling the elongate actuator proximally until the first expandable member contacts one of the adjacent anatomical structures and the second expandable member contacts the other of the adjacent anatomical structures, the providing includes measuring a distance that the first expandable member and the second expandable member moved relative to the elongate actuator, the distance that the first expandable member and the second expandable member moved correlates to the distance between the anatomical structures.

20. The method of claim 14, further comprising:

based on the providing, selecting an implant to be inserted between the adjacent anatomical structures.

* * * * *